United States Patent [19]

Seamons et al.

[11] Patent Number: 5,059,402
[45] Date of Patent: Oct. 22, 1991

[54] CONTACT LENS DISINFECTION UNIT

[76] Inventors: Kenneth R. Seamons, 2789 Saddlebrook Way, Marietta, Ga. 30064; Peter J. Gillespie, 4171 Gunnin Rd., Norcross, Ga. 30092

[21] Appl. No.: 231,526

[22] Filed: Aug. 12, 1988

[51] Int. Cl.$^5$ .............................................. A61L 2/00
[52] U.S. Cl. .................................... 422/300; 422/297; 422/301; 206/5.1
[58] Field of Search ....................... 422/300, 297, 301; 206/5.1

[56] References Cited

U.S. PATENT DOCUMENTS

| | | | |
|---|---|---|---|
| 4,011,941 | 3/1977 | Parsons | 206/5.1 |
| 4,143,116 | 3/1979 | Meletzer | 422/116 |
| 4,396,583 | 8/1983 | LeBouef | 422/301 |
| 4,637,919 | 1/1987 | Ryder et al. | 422/300 |

FOREIGN PATENT DOCUMENTS

| | | |
|---|---|---|
| 082798 | 6/1983 | European Pat. Off. . |
| 0155505 | 9/1985 | European Pat. Off. . |
| 0209971 | 1/1987 | European Pat. Off. . |
| 0218539 | 4/1987 | European Pat. Off. . |
| 0251211 | 1/1988 | European Pat. Off. . |
| 2361118 | 3/1978 | France . |
| 1531035 | 11/1978 | United Kingdom . |
| WO86/07264 | 12/1986 | World Int. Prop. O. . |

*Primary Examiner*—Robert J. Warden
*Assistant Examiner*—Laura E. Collins
*Attorney, Agent, or Firm*—Wenderoth, Lind & Ponack

[57] ABSTRACT

A contact lens disinfection unit constituted by a container, a cap detachably mounted on the container, and a lens and catalyst block holder mounted on and depending from the cap and extending into the container when the cap is mounted on the container. The holder engages a pair of contact lens for holding the contact lenses with the surfaces thereof exposed to the space around the holder, and has structure for holding catalyst block on the holder in a position for circulation of a disinfectant solution, from the space around the holder over the catalyst block. The catalyst block can be detachably held so that it can be replaced when the catalyst is depleted.

24 Claims, 6 Drawing Sheets

CONTACT LENS DISINFECTION UNIT

The present invention relates to a contact lens disinfection unit, and more particularly to such a unit in which contact lenses can be held for circulating a disinfecting solution thereover for disinfecting them.

BACKGROUND OF THE INVENTION

It is particularly important that so-called soft contact lenses be kept sterile, because they tend to cause infections in the eye if they are not periodically disinfected.

Past methods of disinfecting such lenses have involved such cumbersome steps as boiling them for a predetermined length of time, or alternatively immersing them in a disinfecting solution, particularly hydrogen peroxide solutions, removing them from the solution, and immersing them again in a neutralizing solution or a rinsing solution. This system requires a lens disinfection unit which can be cumbersome to use, since it can require the insertion and removal of the holder for the lenses several times during the course of the process. Moreover, the process has created certain difficulties, since the hydrogen peroxide disinfecting solution and the neutralizing or rinsing solutions have frequently been simple clear solutions, and the user can, on occasion, forget which of the solutions has been used, particularly where the lenses are immersed in the disinfecting solution and left standing for a period of time, during which the user forgets whether the lenses have been neutralized or rinsed. Needless to say, it is extremely dangerous to insert into the eye a contact lens which has been removed directly from the hydrogen peroxide disinfecting solution, since such a disinfecting solution is highly irritating to the eye.

There is a need for simple lens disinfection unit which is easy to use and which will automatically neutralize a disinfecting solution.

OBJECTS AND BRIEF SUMMARY OF THE INVENTION

It is an object of the present invention to provide a contact lens disinfection unit for use with a contact lens disinfecting solution which is simple and easy to use and which automatically neutralizes the disinfecting solution after a certain period of time.

It is a further object of the invention to provide such a contact lens disinfection unit which will hold the lenses in position so that the disinfecting solution will circulate over them during the time they are being disinfected and neutralized, so as to effectively disinfect all surfaces of the contact lenses.

It is a still further object of the invention to provide such a lens disinfection unit in which a catalyst block for neutralizing the disinfecting solution can be easily replaced when its catalyst has become ineffective for neutralizing the disinfecting solution.

To this end, the contact lens disinfection unit of the present invention comprises a container with a cap detachably mounted thereon, and a lens and catalyst block holder mounted on and depending from the cap and extending into the container when the cap is mounted on the container. The holder has means for engaging a pair of contact lenses for holding the contact lenses with the surfaces thereof exposed to the space around the holder, and means is provided for holding a catalyst block on the holder in a position for circulation of a disinfecting solution from the space around the holder and over the catalyst block.

BRIEF DESCRIPTION OF THE DRAWINGS

The invention will be described in further detail in connection with the accompanying drawings, in which.

DETAILED DESCRIPTION OF THE DRAWINGS

Figure 1:
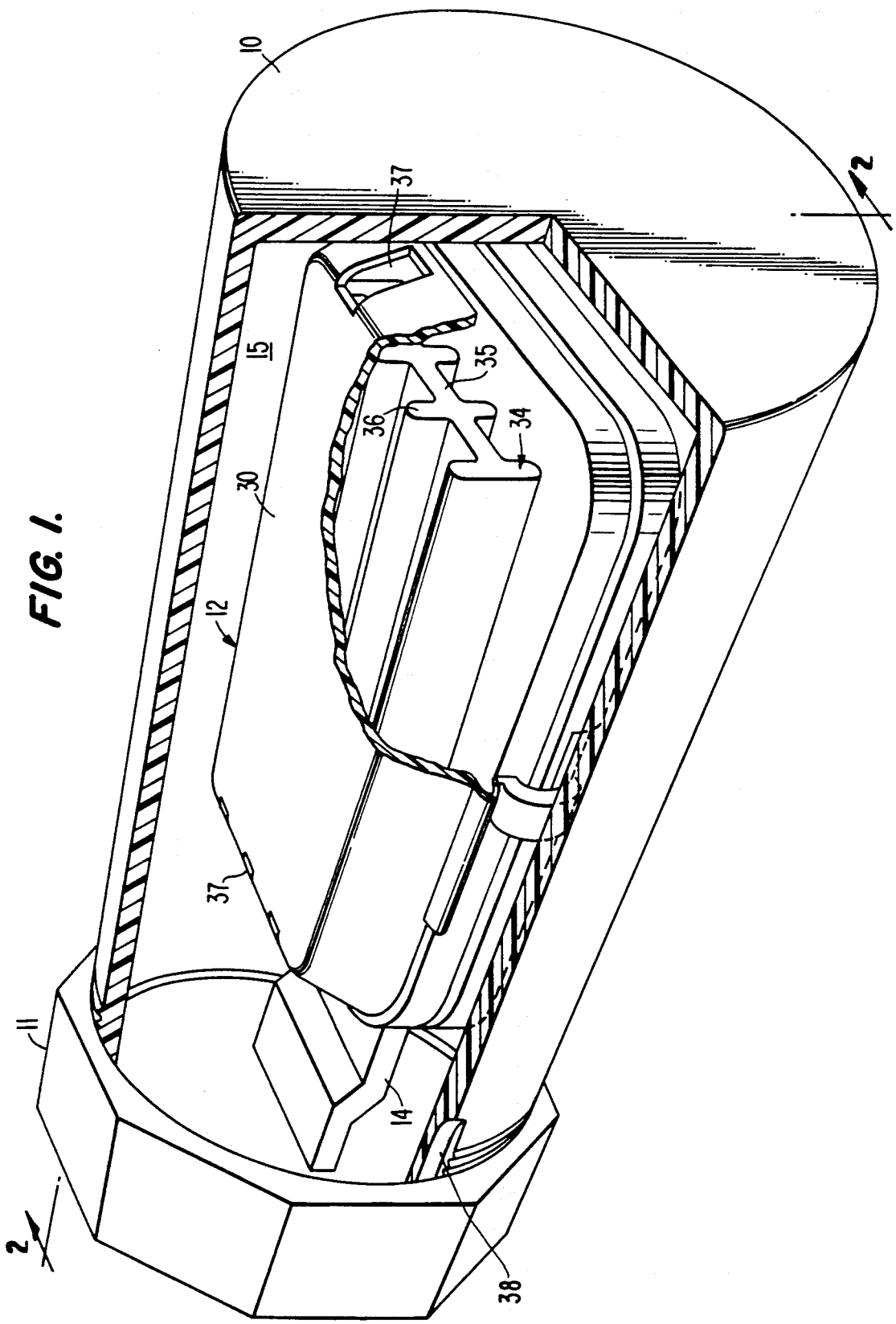
FIG. 1 is a perspective view, partly broken away, of a contact lens disinfection unit according to one embodiment of the invention.

The contact lens disinfection unit according to a first embodiment as shown in FIGS. 1-4, has a container 10, here shown as a cylindrical plastic container with a threaded neck, and a cap 11 detachably mounted on the container 10. In the embodiment shown, the attachment is by means of conventional threaded engagement, but any other conventional type of engagement, such as a snap fit, can be employed. Further, while the container is shown as being cylindrical, it can have any other convenient shape as desired.

A lens and catalyst block holder 12 is provided which as a base member 13 from which a stem 14 extends. The stem is mounted on the underside of the cap 11, so that with the container 10 in an erect position, the lens and catalyst block holder 12 depends from and extends into the container. The size of the container is such that a space 15 is left around the periphery of the lens and catalyst block holder 12 for holding a disinfecting solution.

Figure 4:
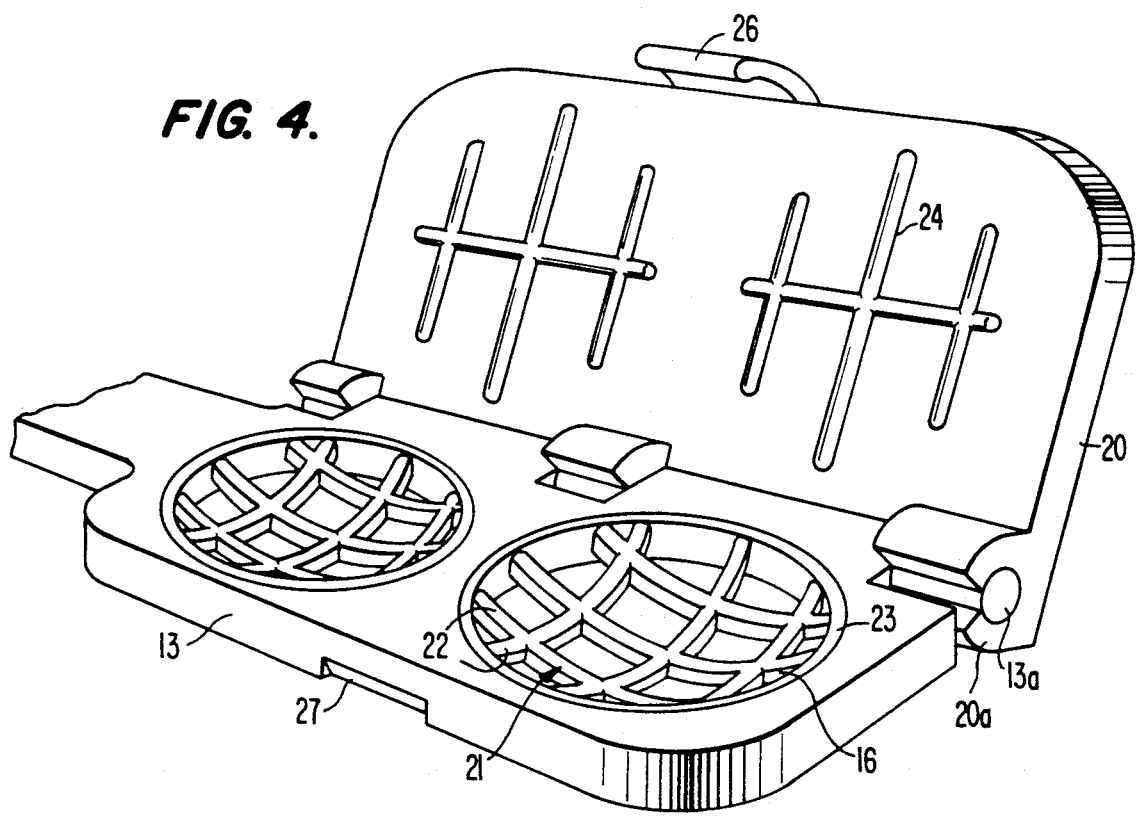
FIG. 4 is a perspective view of the lens and catalyst block holder of FIGS. 1-3, with the members in the open position.

The base member 13 has a pair of holes 16 therethrough which contain a pair of lens engaging means in the form of lens receiving baskets 21 which extend concavely from the surface of the base member 13 which is uppermost in FIGS. 1 and 4. The lens receiving baskets 21 are constituted by a plurality of grid members 22 intersecting each other at generally right angles, and a raised edge 23 extending around the aperture.

Figure 2:
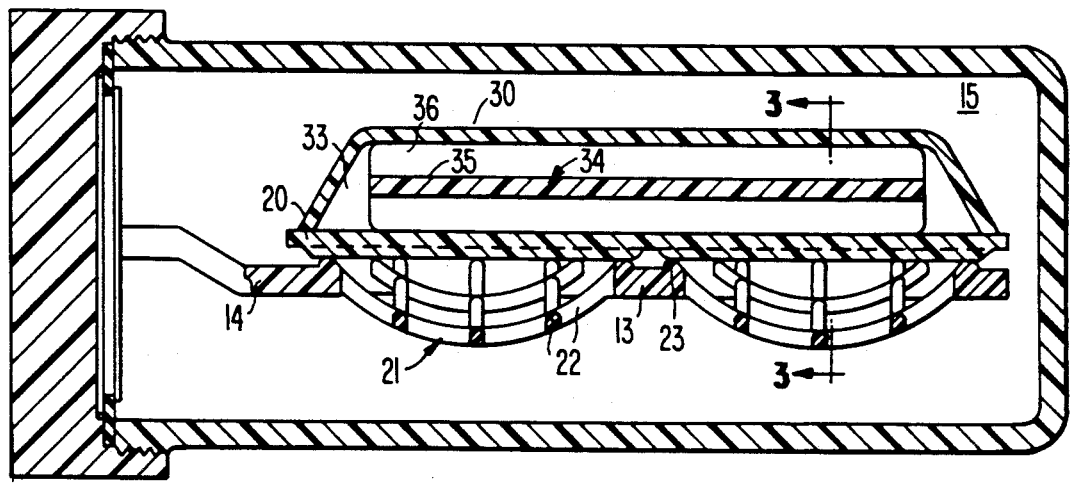
FIG. 2 is a sectional view taken along line 2—2 of FIG. 1.
Figure 3:
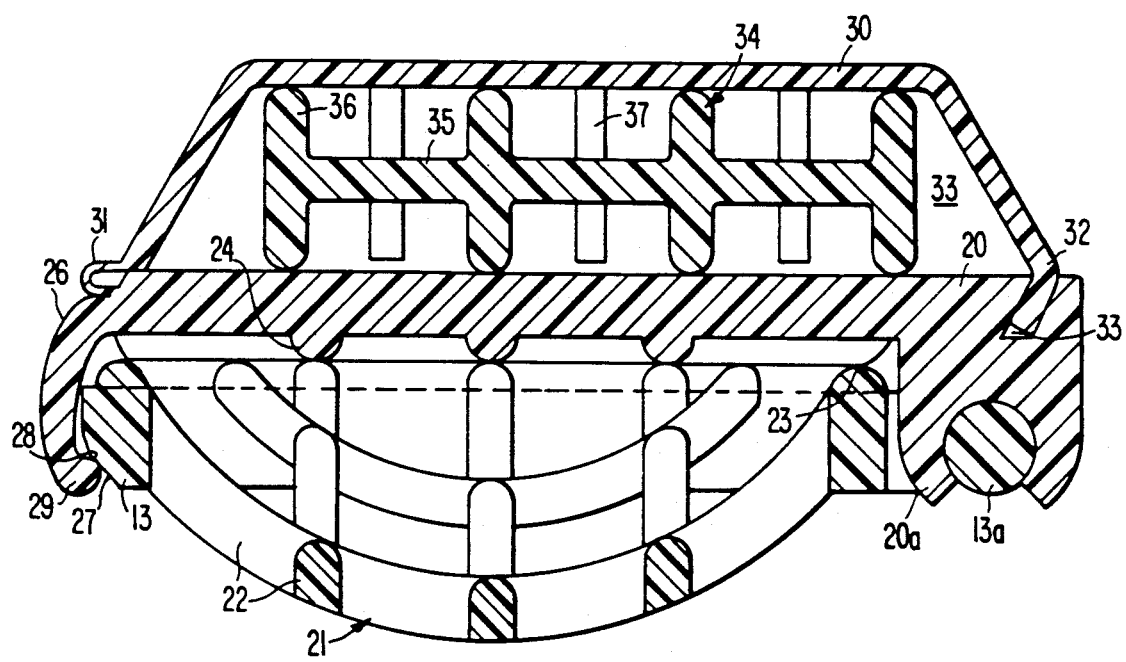
FIG. 3 is a section taken along line 3—3 of FIG. 2.

The lens and catalyst block holder further comprises a top member 20, and the base member 13 and top member 20 are hinged to each other by a hinge means, here shown in the form of hinge pins 13a on the base member 13 and hinge members 20a on the top member 20. The hinge permits the top member 20 and base member 13 to be folded so that the opposed surfaces are basically against each other, in the position as shown in FIGS. 1 and 2.

The top member 20 has a pair of lens engaging means thereon in the form of ribs 24 extending at right angles to each other, and positioned on the surface of the top member 20 which will be opposed to the top surface of the base member 13 when the top member 20 and the base member 13 are folded together, and opposed to the lens receiving baskets 21, so as to enable contact lenses placed in the lens receiving baskets 21 to be held in position in the lens and catalyst block holder 12.

Means is provided on the base member and top member for securing them in the folded over condition, and in the embodiment of FIGS. 1–4, this means is comprised of a closure member 26 depending from the free edge of the top member 20 opposite the edge having the hinge members 20a thereon, which is engageable with a closure member receiving recess 27 in the corresponding edge of the base member 21. As can be seen from FIG. 3, the outwardly facing surface of the recess 27 has a sharp break 28 therein, and the inwardly facing surface of the closure member 26 has a nose 29 thereon which fits under the sharp break 28 for holding the top and base members 20 and 13 in the closed or folded over position.

The contact lens disinfection unit has a means for holding a catalyst block 34 in a position for circulation of a disinfectant solution from the space 15 within the container 10 over the catalyst block 34. In the embodiment of FIGS. 1–4, this means is constituted by a catalyst block cover 30 which is hinged by a hinge 31 integral with the top member 20 along one edge thereof, and having a closure retainer 32 at the opposite edge thereof engaged in a recess 33 in the top member 20 for holding the catalyst block cover in place. The catalyst block cover has a shape for defining with the outer surface of the top member 20 a catalyst block recess 33. Openings 37 are provided in the catalyst block cover 30 for permitting circulation of disinfecting solution through the space 33 over the surfaces of the catalyst block 34. In the present embodiment, these openings are provided in the end walls of the cover 30.

The catalyst block 34 as shown in FIGS. 1–4 is constituted by a block base 35 and ribs 36 which project in opposite directions from the base 35, and which extend generally longitudinally of the top member 20. The size is such that the cover 30 engages the outer ends of the ribs 36 and presses the catalyst block 34 against the outer surface of the cover 30 for holding it in position in the space 33.

While the embodiment of FIGS. 1–4 has the lens receiving baskets 21 in the base member 13 and the ribs 24 on the top member 20, it will be appreciated that these positions can be reversed, i.e. the lens receiving baskets 21 can be in the top member 20 and the projecting ribs 24 can be on the base member 13. Further, the openings 37 in the catalyst block cover 30 can have different shapes and can be located anywhere in the cover so long as they permit circulation of the disinfecting solution along the base 35 and ribs 36 of the catalyst block.

Further, the catalyst block need not have the exact shape as shown, but can have any convenient shape, and the catalyst block cover can be given a shape such that it will hold the catalyst block against the outer surface of the top member 20.

Finally, while the catalyst block cover 30 has been shown as being on the outer surface of the top member 20, it can, alternatively be on the outer surface of the base member 13 and hold the catalyst block 34 against the bottom of base member 13.

In use, the catalyst block 34 is provided in the catalyst block space 33, and has a catalyst (not shown) coated thereon which, when the disinfecting solution is passed over the catalyst, will neutralize the disinfecting solution. The cap 11 is removed from the container 10, thus drawing the lens and catalyst block holder 12 out of the container 10, and the top member 20 is pivoted away from the base member 13 by releasing the closure member 26, thus opening the top member to the position as shown in FIG. 4. Contact lenses are then placed with the convex sides down in the lens receiving baskets 21, and the top member 20 is then closed and the closure member 26 engaged with the closure member receiving recess 27.

The container 10 is then substantially filled with the the disinfecting solution, and the lens and catalyst block holder 12 are inserted into the container 10 and the cap 11 engaged with the container.

The disinfecting solution flows around the contact lenses through the grid members 22 of the baskets 21, and past the ribs 24, disinfecting the lenses. It also comes in contact with the catalyst on the catalyst block 34, and the neutralization starts In the typical system, neutralization produces gas, which tends to raise to the top of the container 10 when the container is in its normal position, i.e. standing upright with the cap 11 at the top. This induces circulation of the disinfectant downwardly along the base member 13 and the face of the top member 20 facing the base member 13, and over the surfaces of the contact lenses held between the rib members 22 of the baskets 21 and the ribs 24. The circulation is further induced over the surfaces of the block ribs 36 and the block base 35 along the surfaces thereof, by the flow of the disinfectant solution through the circulating openings 37. At such time as the neutralization is complete, generation of gas will cease, and the lenses will then be suitable for insertion into the eyes.

A gas escape groove 38 can be provided in the open end of the container 10 for escape of gases during the neutralization process.

Figure 5:
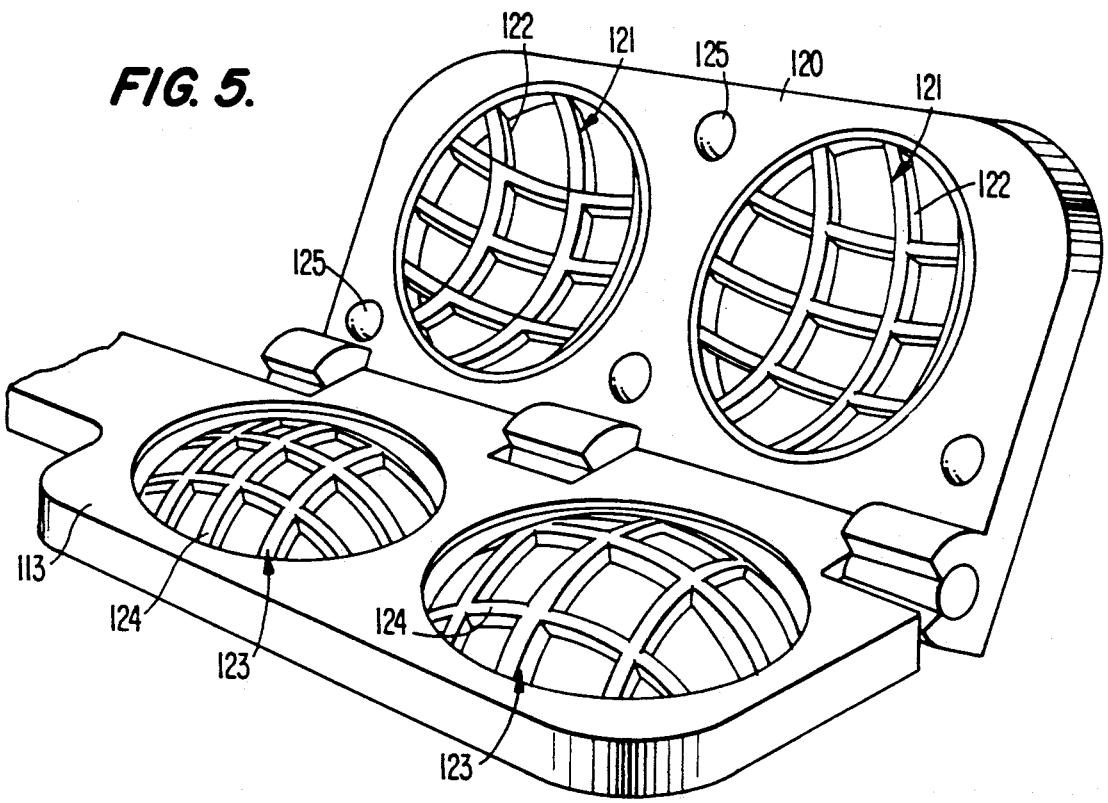
FIG. 5 is a view similar to FIG. 4 of a lens and catalyst block holder according to a second embodiment of the invention.

As shown in FIG. 5, the means for engaging the pair of contact lenses in both the base member and the top member can be lens receiving baskets. As shown, the base member 113 has two apertures therein, in which are provided inverted lens engaging baskets 123 having inverted grid members 124 which are convex from the upper surface of the base member 113. At corresponding positions on the top member 120 are lens receiving baskets 121 having grid members 122 which are concave with respect to the face of the top member 120 which faces the base member when the members are folded together. The grid members 122 are, when the members 113 and 120 are folded together, spaced slightly from the grid members 124 so as to accommodate contact lenses therebetween. This spacing is insured by a plurality of spacing knobs 125 on the surface of the top member 120 facing the upper surface of the base member 113.

As will be appreciated, the lens baskets 123 and 121 can be interchanged, i.e. the concave lens baskets 121 can be provided in the base member 113, and the inverted baskets 123 can be provided in the top member 120. Likewise, the spacing knobs 125 can be provided on either of the faces of the base member or the top member which is opposed to the other member when the members are folded together.

Some modification of the shape of the catalyst block may be necessary to accommodate any portions of the lens engaging baskets 121 which project above the upper surface of the top member 120.

The use of this embodiment is the same as the embodiment of FIGS. 1-4, except that the disinfecting solution will circulate through the lens engaging baskets 121 in the top member into the space 33 in which the catalyst block is located, or, where the catalyst block is on the outside of the base member 113, through the baskets 123 therein.

In both embodiments, when the catalyst coated on the catalyst block becomes inactive, the catalyst block can be replaced by opening the cover 30.

Figure 6:
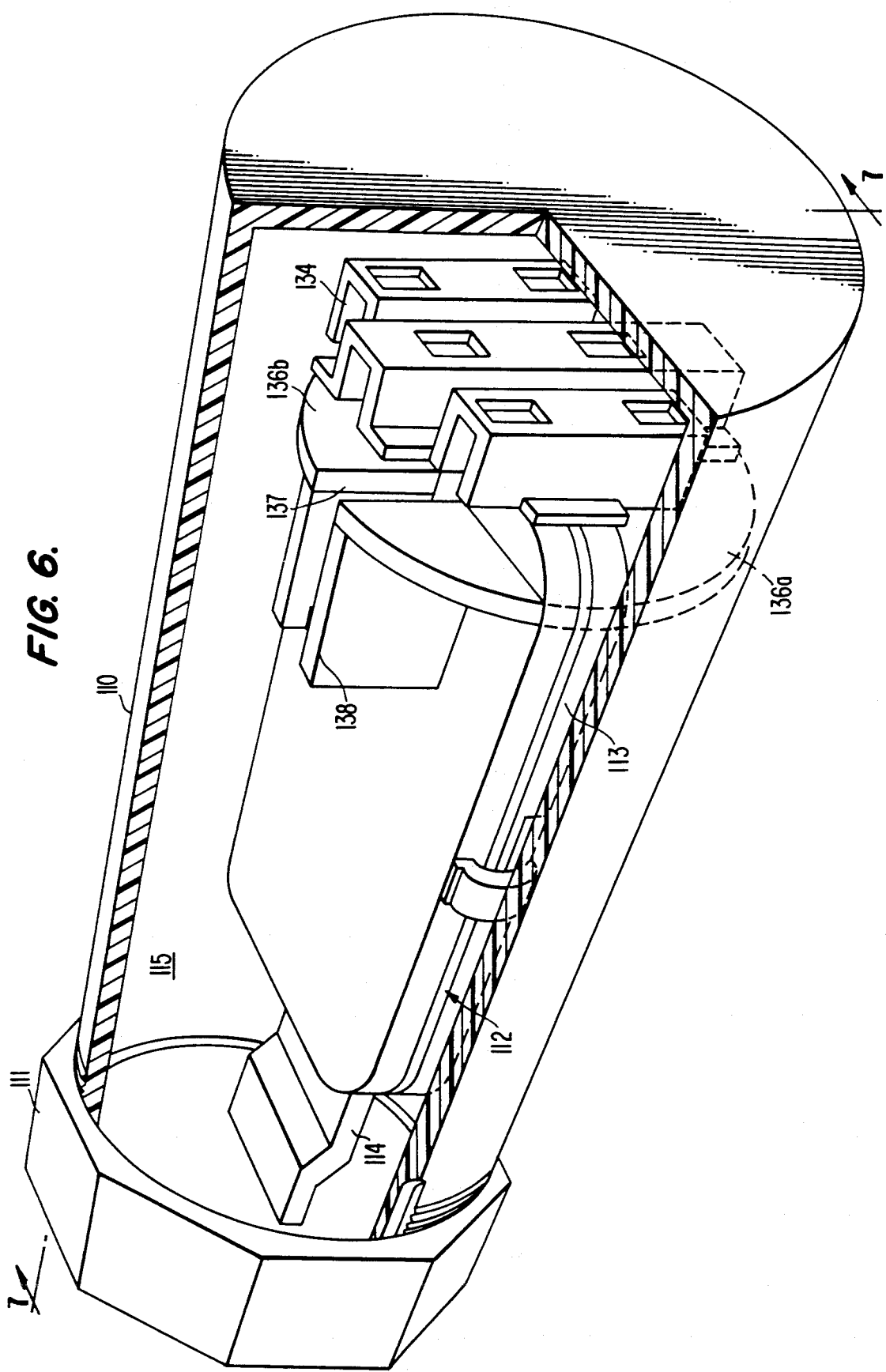
FIG. 6 is a perspective view similar to FIG. 1 of a contact lens disinfection unit according to a third embodiment of the invention.
Figure 7:
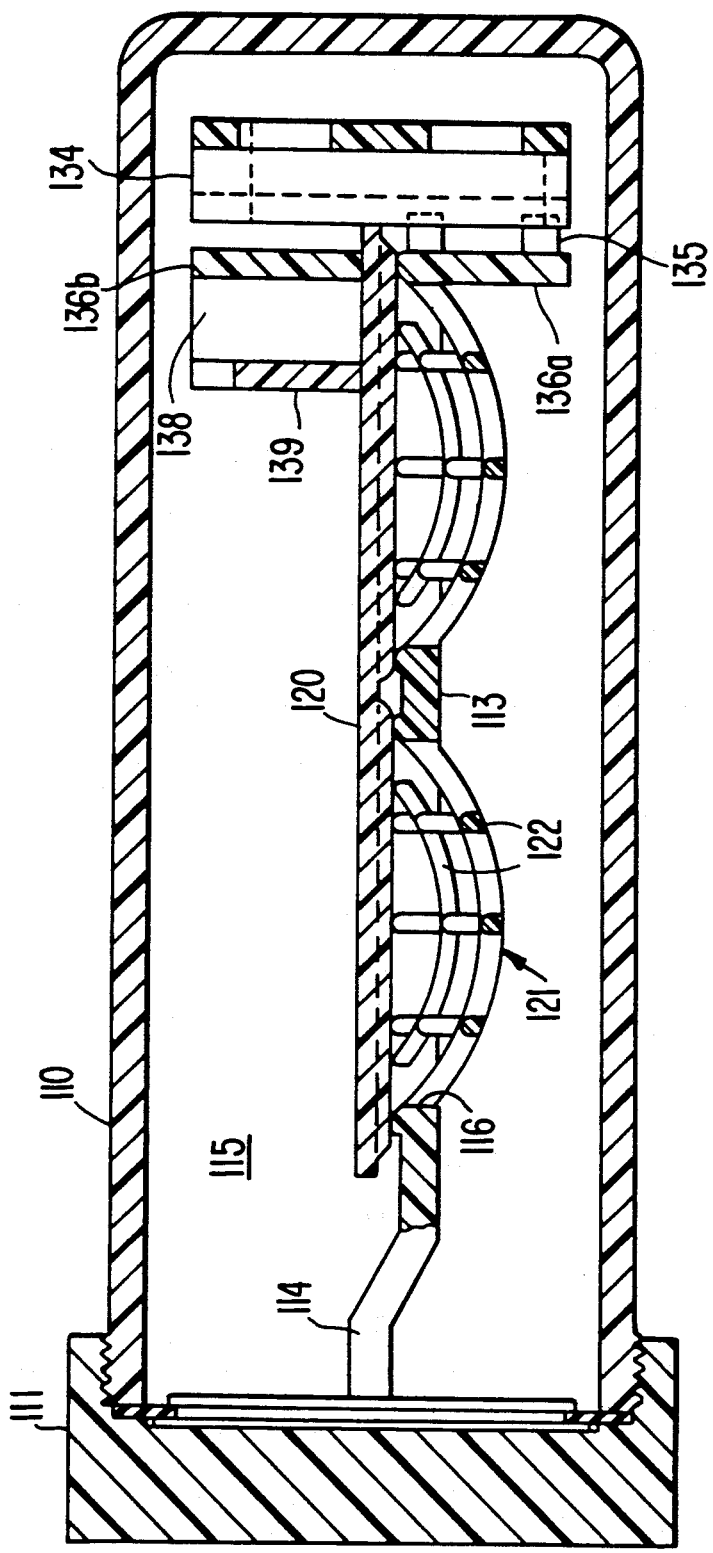
FIG. 7 is a longitudinal sectional view taken along line 7—7 of FIG. 6.

The contact lens disinfection unit according to a further embodiment as shown in FIGS. 6 and 7, similar to the embodiment of FIGS. 1-4, has the container 110, and the cap 111 detachably mounted on the container 110.

The lens and catalyst block holder 112 is provided which as the base member 113 from which the step 114 extends. The stem is mounted on the underside of the cap 111, so that with the container 110 in an erect position, the lens and catalyst block holder 112 depends from and extends into the container. The size of the container is such that a space 115 is left around the periphery of the lens and catalyst block holder 112 for holding a disinfecting solution.

As in the embodiment of FIGS. 1-4, the base member 113 has a pair of holes 116 therethrough which container the lens receiving baskets 121 which extend concavely from the surface of the base member 113 which is uppermost in FIGS. 6 and 7. The lens receiving baskets 121 are constituted by the plurality of grid members 122 intersecting each other at generally right angles.

The lens and catalyst block holder further comprises the top member 120, and the base member 113 and top member 120 are hinged to each other by a hinge means the same as in the embodiment of FIGS. 1-4. The hinge permits the top member 120 and base member 113 to be folded so that the opposed surfaces are basically against each other, in the position as shown in FIGS. 6 and 7.

The top member 20 has the lens engaging ribs 124 the same as the embodiment of FIGS. 1-4, and the means on the base member and top member for securing them in the folded over condition, as in the embodiment of FIGS. 1-4.

In this embodiment, the catalyst block 134 is mounted at the bottom of the base member 113 for circulation of a disinfectant solution from the space 115 within the container 110 over the catalyst block 134. The catalyst block 134 as shown is in the form of a multi-channeled member having holes therethrough opening generally perpendicularly to the length of the channels, for permitting solution to circulate both along the channels as well as through the holes. However, any shape of catalyst block can be used as long as it fits in the space between the end of the base member 113 and the bottom of the container 110, and has sufficient channels, holes and the like to permit the solution to circulate thereover to accomplish the desired action of the catalyst on the solution.

The catalyst block 134 is detachably mounted on projections 135 which extend in a friction fit into mounting apertures (not visible in the drawings) in the catalyst block, and the projections 135 are in turn provided on a lower disk member 136a which is mounted on the lower end of the base member 113 below the lower of the two baskets 121. The lower disk member is a semicircular disk which has the periphery thereof spaced from the inner surface of the container 110 sufficient to provide a passage for solution to flow past the periphery of the disk member 136a.

An upper disk member 136b is mounted on the top member 120 in substantial alignment with the lower disk member 136a, and is also semicircular and has the periphery spaced from the inner surface of the container 110 to leave a further passage for flow of solution past the upper disk member. It is preferable, for reasons described hereinafter, to provide means for permitting some flow of solution through the upper disk member 136b, and to this end, this embodiment provides a slot 137 in the disk member 136b with side walls 138 extending along the upper surface of the top member 120 and closed at the end toward the cap 111 by a closure wall 139 which is shorter than the walls 138. This permits solution to flow from the catalyst block through the disk member 136b and along the space between the walls 138 and over the closure wall 139.

The disk members 136a and 136b are provided as a shield for the catalyst block 134 between the lens receiving baskets 121 and the catalyst block. This shields the fingers of the user from accidentally contacting the catalyst block 134 while lenses are being placed in or removed from the lens baskets during use of the unit.

When the catalyst is exhausted, the catalyst block 134 can be removed from the projections 135 and replaced by a catalyst block with a fresh coating of catalyst thereon.

The catalyst block could of course be mounted on projections similar to the projections 135 on the upper disk member 136b.

The embodiment of FIGS. 6 and 7 is used in the same way as the embodiment of the earlier figures, and the description of the use will not be repeated.

Figure 8:
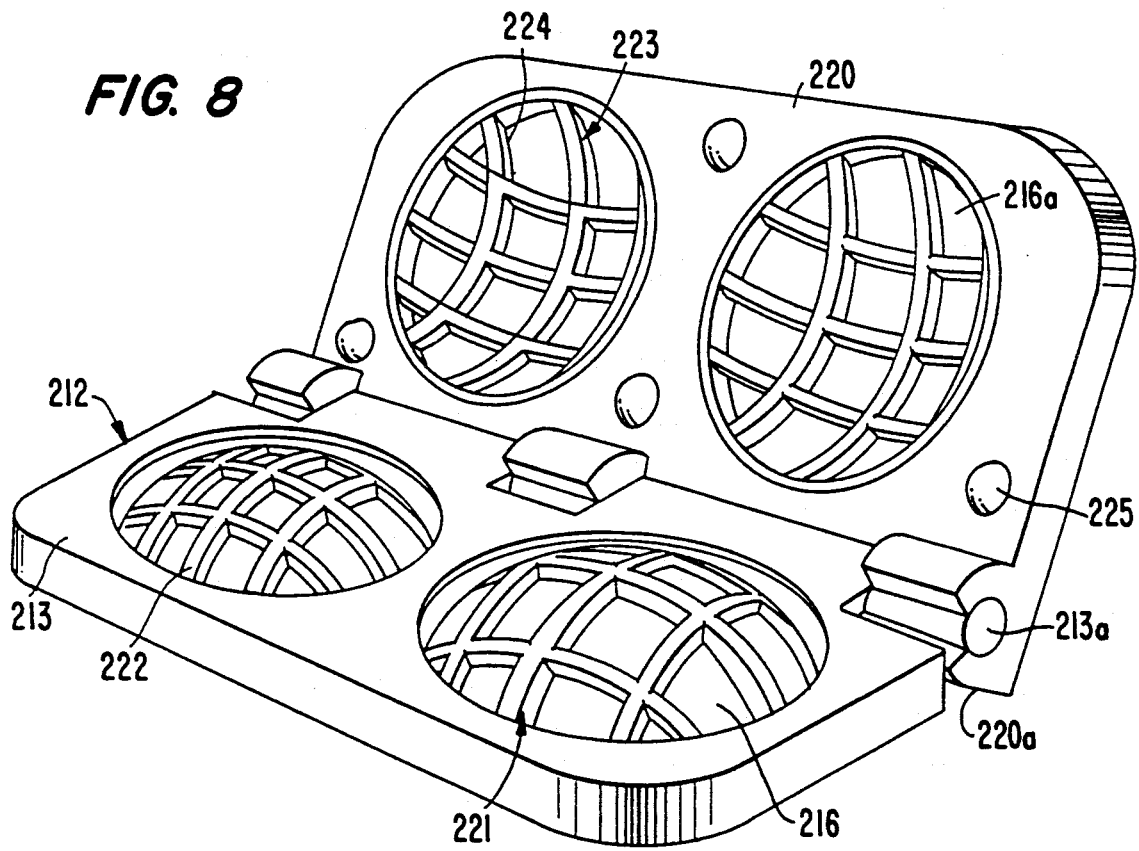
FIG. 8 is a perspective view of a contact lens holder for use in a contact lens disinfection unit.

A separate lens holder 212 is shown in FIG. 8 which can be used with a different type container. It is comprised of a base member 213 which has a pair of holes 216 therethrough which contain a pair of lens engaging means in the form of lens receiving baskets 221 which extend convexly from the surface of the base member 213 which is uppermost in FIG. 8. The lens receiving baskets 221 are constituted by a plurality of grid members 222 intersecting each other at generally right angles.

The lens holder further comprises a top member 220, and the base member 213 and top member 220 are hinged to each other by a hinge means, here shown in the form of hinge pins 213a on the base member 213 and hinge members 220a on the top member 220. The hinge permits the top member 220 and base member 213 to be folded so that the opposed surfaces are basically against each other, similar to the position of the embodiment of FIGS. 1-4 as shown in FIGS. 1 and 2.

The top member 220 has a pair of holes 216a in which are lens engaging means thereon in the form of lens receiving baskets 223 which extend concavely in the surface of the top member. The lens receiving baskets 223 are constituted by a plurality of grid members 224 intersecting each other at generally right angles. The baskets 223 are opposed to the baskets 221 in the top surface of the base member 213 when the top member 220 and the base member 213 are folded together, and the opposed lens receiving baskets 221 and 223 are spaced slightly so as to hold contact lenses placed in the lens receiving baskets in position.

Means can be provided on the base member and top member for securing them in the folded over condition, which is preferably the same as the means 26 and 27 in the embodiment of FIGS. 1–4. Moreover, means in the form of knobs 225 can be provided on one of the members, for example the top member 220, which when the members 213 and 220 are folded together, keep the baskets 221 and 223 spaced slightly so as to accommodate the lenses therebetween.

Similarly, the contact lens holder can have a means (not shown) on top member 220 for holding a catalyst block similar to the catalyst block 34 in FIGS. 1-4 in a position for circulation of a disinfectant solution over the catalyst block and through the baskets 223 over the lenses. Alternatively, the catalyst block can be on the back of the base member 213.

Where the holder has no means for holding a catalyst block, it can be used in a container of any shape which has a catalyst block therein.

It will be seen that there has been provided a contact lens disinfection unit which is simple and easy to use and which automatically neutralizes the disinfecting solution after a certain period of time. The disinfection unit holds the lenses in position in the lens baskets so that the disinfecting solution will circulate over them so as to effectively disinfect the entire surfaces of the contact lenses. The catalyst block 34 can be easily replaced when the catalyst coated thereon is no longer effective for neutralizing the disinfecting solution, so that the unit can be used over and over again.

Although the present invention has fully been described in connection with the preferred embodiments thereof, it is to be noted that various changes and modifications will be apparent to those skilled in the art. Accordingly, such changes and modifications are to be understood as included within the scope of the present invention as defined by the appended claims.

What is claimed is:

1. A contact lens disinfection unit comprising:
   a container;
   a cap detachably mounted on said container;
   a lens and catalyst block holder mounted on and depending from said cap and extending into said container when said cap is mounted on said container, said holder having means for engaging a pair of contact lenses for holding the contact lenses with the surfaces thereof exposed to the space around said holder, and means for holding a catalyst block on said holder in a position for circulation of a disinfectant solution from the space around said holder over the catalyst block.

2. A contact lens disinfection unit as claimed in claim 1 in which said lens and catalyst block holder comprise a base member having a pair of lens engaging means thereon for engaging a pair of contact lenses, a top member having a pair of lens engaging means thereon for engaging a pair of contact lenses, said base member and said top member being hinged to each other and said lens engaging means on said base member and said top member being opposed to each other when said base member and said top member are folded against each other for holding a pair of contact lenses therebetween, means on one of said base member and said top member for engaging the other for securing them in the folded over condition, and said catalyst block holding means being on one of said base member and said top member.

3. A contact lens disinfection unit as claimed in claim 2 in which said lens engaging means on one of said members comprises a pair of lens receiving baskets having a plurality of grid members extending concavely from the surface of said member which faces the other member when said members are folded against each other and having spaces therebetween, and said lens engaging means on the other of said members comprises a pair of sets of ribs projecting from the surface of said other member which opposes the one member when said members are folded against each other, said ribs being opposed to said baskets when said members are folded against each other.

4. A contact lens disinfection unit as claimed in claim 3 in which said one member has a pair of holes therethrough in which said lens receiving baskets are positioned.

5. A contact lens disinfection unit as claimed in claim 2 in which said lens engaging means on said base member comprises a pair of lens receiving baskets having a plurality of grid members extending concavely from the upper surface of said base member and having spaces therebetween, and said lens engaging means on said top member comprises a pair of sets of ribs projecting from the bottom surface of said top member which opposes the top surface of said base member when said top member and said base member are folded against each other, said ribs being opposed to said baskets when said top member and said base member are folded against each other.

6. A contact lens disinfection unit as claimed in claim 5 in which said base member has a pair of holes therethrough in which said lens receiving baskets are positioned.

7. A contact lens disinfection unit as claimed in claim 2 in which said lens engaging means on one of said members comprises a pair of inverted lens engaging baskets having a plurality of grid members extending convexly from the surface of said member which faces the other member when said members are folded against each other and having spaces therebetween, and said lens engaging means on said other member comprises a pair of lens receiving baskets having a plurality of grid members extending concavely from the surface of said other member which opposes said one member when said members are folded against each other and having spaces therebetween, said baskets being opposed to each other when said members are folded against each other.

8. A contact lens disinfection unit as claimed in claim 7 in which each of said members has a pair of holes therethrough in which said respective lens engaging baskets and said lens receiving baskets are positioned.

9. A contact lens disinfection unit as claimed in claim 2 in which said lens engaging means on said base member comprises a pair of inverted lens engaging baskets having a plurality of grid members extending convexly from the upper surface of said base member and having spaces therebetween, and said lens engaging means on said top member comprises a pair of lens receiving baskets having a plurality of grid members extending concavely from the bottom surface of said top member which opposes the top surface of said base member when said top member and said base member are folded against each other and having spaced therebetween, said baskets being opposed to each other when said top member and said base member are folded against each other.

10. A contact lens disinfection unit as claimed in claim 9 in which said base member and said top member each having a pair of holes therethrough in which the respective lens engaging baskets and lens receiving baskets are positioned.

11. A contact lens disinfection unit as claimed in claim 9 in which said top cover member has spacing knobs on the bottom surface thereof for engaging the top surface of said base member for slightly spacing the ribs of said baskets from each other for accommodating contact lenses therebetween.

12. A contact lens disinfection unit as claimed in claim 2 in which said catalyst block holding means comprises a catalyst block cover detachably engaged with one of said member and defining a space within said cover when it is engaged with said member for holding a catalyst block therein, said cover having apertures therein for permitting circulation of a disinfectant through said space.

13. A contact lens disinfection unit as claimed in claim 12 in which said catalyst block cover is hinged at one side to said member and closure means for holding the other side of said catalyst block cover to said member.

14. A contact lens disinfection unit as claimed in claim 2 in which said catalyst block holding means comprises a catalyst block cover detachably engaged with said top member and defining a space within said cover when it is engaged with said top member for holding a catalyst block therein, said cover having apertures therein for permitting circulation of a disinfectant through said space.

15. A contact lens disinfection unit as claimed in claim 14 in which said catalyst block cover is hinged at one side to said top member and closure means for holding the other side of said catalyst block cover to said top member.

16. A contact lens disinfection unit as claimed in claim 2 in which said catalyst block holding means comprises means for detachably holding a catalyst block mounted on one of said members at the end thereof remote from said cap.

17. A contact lens disinfection unit as claimed in claim 16 in which said means for detachably holding a catalyst block is mounted on said base member.

18. A contact lens disinfection unit as claimed in claim 16 in which said means for detachably holding a catalyst block is mounted on said top member.

19. A contact lens disinfection unit as claimed in claim 16 further comprising a disk means mounted on said base member and said top member between said members and said catalyst block for shielding said catalyst block 20. A contact lens holder for holding contact lenses in a disinfection unit, comprising:
a first member and a second member hinged to said first member, said members being foldable together, said first member having a pair of inverted lens engaging baskets having a plurality of grid members extending convexly from the surface of said first member which faces the other member when said members are folded against each other and having spaces therebetween, and said second member having a pair of lens receiving baskets having a plurality of grid members extending concavely from the surface of said other member which opposes said one member when said members are folded against each other and having spaces therebetween, said baskets being opposed to each other when said members are folded against each other.

21. A contact lens disinfection unit as claimed in claim 20 in which each of said members has a pair of holes therethrough in which said respective lens engaging baskets and said lens receiving baskets are positioned.

22. A contact lens disinfection unit as claimed in claim 20 in which said one of said members has spacing knobs on the surface thereof for engaging the exposed surface of said other member for slightly spacing the ribs of said baskets from each other for accommodating contact lenses therebetween.

23. A contact lens disinfection unit as claimed in claim 20 further having a catalyst block holding means on the side of one of said members which faces away from the other member when the members are folded against each other 24. A contact lens disinfection unit comprising:
a container;
a cap detachably mounted on said container;
a lens holder mounted in and extending into said container, said holder having means for engaging at least one contact lens for holding the contact lens with the surfaces thereof exposed to the space around said holder, and a catalyst block in said container in a position for circulation of a disinfectant solution from the space around said holder over the catalyst block.

* * * * *